United States Patent
Shore et al.

(10) Patent No.: US 12,025,602 B2
(45) Date of Patent: Jul. 2, 2024

(54) AUTONOMOUS CROP MONITORING SYSTEM AND METHOD

(71) Applicant: AgroScout Ltd., Misgav (IL)

(72) Inventors: Simcha Shore, Eshchar (IL); Ilan Ehrenfeld, Ariel (IL); Ido Bar-Av, Moshav Yevul (IL); Shahar Harari, Tel Aviv (IL)

(73) Assignee: AgroScout Ltd., Misgav (IL)

( * ) Notice: Subject to any disclaimer, the term of this patent is extended or adjusted under 35 U.S.C. 154(b) by 459 days.

(21) Appl. No.: 17/418,846

(22) PCT Filed: Jan. 8, 2020

(86) PCT No.: PCT/IL2020/050029
§ 371 (c)(1),
(2) Date: Jun. 28, 2021

(87) PCT Pub. No.: WO2020/144683
PCT Pub. Date: Jul. 16, 2020

(65) Prior Publication Data
US 2022/0065835 A1 Mar. 3, 2022

Related U.S. Application Data

(63) Continuation of application No. 16/242,012, filed on Jan. 8, 2019, now abandoned.

(51) Int. Cl.
*G01N 33/00* (2006.01)
*A01G 13/00* (2006.01)
(Continued)

(52) U.S. Cl.
CPC ......... *G01N 33/0098* (2013.01); *A01G 13/00* (2013.01); *A01N 25/00* (2013.01);
(Continued)

(58) Field of Classification Search
CPC .... G01N 33/0098; G06V 20/20; A01G 13/00; A01N 25/00; B64C 39/024; B64U 2101/00; G06Q 50/02
See application file for complete search history.

(56) References Cited

U.S. PATENT DOCUMENTS

| 9,113,590 B2 | 8/2015 | Johnson |
| 9,213,905 B2 * | 12/2015 | Lange .................... G06V 20/58 |

(Continued)

FOREIGN PATENT DOCUMENTS

| CN | 103523224 | 1/2014 |
| CN | 103523225 | 1/2014 |

(Continued)

OTHER PUBLICATIONS

Dunning, "Drones that detect early plant disease could save crops", Phys Org, Apr. 26, 2017, pp. 1-3.
(Continued)

*Primary Examiner* — Gregory M Desire
(74) *Attorney, Agent, or Firm* — PEARL COHEN ZEDEK LATZER BARATZ LLP (57) ABSTRACT

A system for autonomous crop monitoring, the system comprising a mobile platform having one or a plurality of imaging devices configured to autonomously travel a path to scan a plurality of inspection regions in a field of crop and obtain images of the inspection regions; and a processor configured to analyze the acquired images to detect an agricultural condition that requires attention (ACRA) and determine the location of that ACRA.

2 Claims, 5 Drawing Sheets

(51) Int. Cl.
*A01N 25/00* (2006.01)
*B64C 39/02* (2023.01)
*G06K 9/00* (2022.01)
*G06V 20/20* (2022.01)
*B64U 101/00* (2023.01)
*G06Q 50/02* (2012.01)

(52) U.S. Cl.
CPC ............ *B64C 39/024* (2013.01); *G06V 20/20* (2022.01); *B64U 2101/00* (2023.01); *G06Q 50/02* (2013.01)

(56) References Cited

U.S. PATENT DOCUMENTS

| | | | |
|---|---|---|---|
| 10,182,214 B2 * | 1/2019 | Gornik | H04N 7/185 |
| 10,234,439 B2 * | 3/2019 | Sutton | G06V 20/188 |
| 10,255,670 B1 | 4/2019 | Wu et al. | |
| 10,568,316 B2 * | 2/2020 | Gall | A01B 79/005 |
| 10,627,386 B2 | 4/2020 | Saez et al. | |
| 10,660,277 B2 * | 5/2020 | McCall | G06V 10/82 |
| 10,721,859 B2 | 7/2020 | Wu et al. | |
| 10,827,672 B2 * | 11/2020 | Cutter | B64C 39/024 |
| 10,845,301 B2 * | 11/2020 | Ni | G01N 21/314 |
| 10,939,606 B2 * | 3/2021 | Ackerman | G05D 1/0225 |
| 11,319,067 B2 * | 5/2022 | Yanagishita | A01G 7/00 |
| 2004/0034450 A1 | 2/2004 | Seal et al. | |
| 2008/0046130 A1 | 2/2008 | Faivre et al. | |
| 2013/0011011 A1 | 1/2013 | Fryshman | |
| 2014/0168412 A1 | 6/2014 | Shulman et al. | |
| 2014/0303814 A1 | 10/2014 | Burema et al. | |
| 2015/0278640 A1 | 10/2015 | Johnson et al. | |
| 2016/0050840 A1 | 2/2016 | Sauder et al. | |
| 2016/0176542 A1 | 6/2016 | Wilkins | |
| 2016/0202227 A1 | 7/2016 | Mathur et al. | |
| 2016/0216245 A1 | 7/2016 | Sutton | |
| 2016/0223506 A1 | 8/2016 | Shriver et al. | |
| 2016/0334276 A1 | 11/2016 | Pluvinage | |
| 2017/0027155 A1 | 2/2017 | Ehrlich et al. | |
| 2017/0199528 A1 | 7/2017 | Detweiler et al. | |
| 2017/0372137 A1 | 12/2017 | Kumar | |
| 2020/0217830 A1 | 7/2020 | Shore et al. | |
| 2023/0029636 A1 * | 2/2023 | Faers | B64U 10/13 |

FOREIGN PATENT DOCUMENTS

| | | |
|---|---|---|
| CN | 203528823 | 4/2014 |
| CN | 204142639 | 2/2015 |
| CN | 104554726 | 4/2015 |
| WO | WO 2016/065071 | 4/2016 |
| WO | WO 2016/110832 | 7/2016 |
| WO | WO 2016/123201 | 8/2016 |
| WO | WO 2017/004074 | 1/2017 |
| WO | WO 2017/021753 | 2/2017 |
| WO | WO 2017/077543 | 5/2017 |
| WO | WO 2018/136875 | 7/2018 |

OTHER PUBLICATIONS

Mahlein, "Plant Disease Detection by Imaging Sensors-Parallels and Specific Demands for Precision Agriculture and Plant Phenotyping", The American Phytopathological Society, Feb. 2016, pp. 241-251.

"Detecting disease via drones", Citrograph Magazine, Fall 2015, Citrus Research Board.

Honan, "Drones could be the answer to early disease detection in banana crops", ABC Rural, ABC News, Jul. 17, 2016, pp. 1-2.

Tammen, "Multimillion-dollar project using unmanned aerial systems to detect emerging pest insects, diseases in food crops", K-State News, Mar. 18, 2015.

Albetis, et al., "Detection of *Flavescence dorée* Grapevine Disease Using Unmanned Aerial Vehicle (UAV) Multispectral Imagery", Remote Sens., 2017, 9-4:308, pp. 1-20.

Smigaj, et al., "UAV-Borne Thermal Imaging for Forest Health Monitoring: Detection of Disease-Induced Canopy Temperature Increase", The International Archives of the Photogrammetry, Remote Sensing and Spatial Information Sciences, 2015, vol. XL-3/3, La Grande Motte, France, pp. 349-354.

Di Gennaro, et al., "The drone application for monitoring and detection of esca disease in the vineyard"; Università degli Studi di Firenze, Consiglio Nazionale delle Ricerche, Istituto di Biometeorologia.

Hunt, et al., "Acquisition of NIR-Green-Blue Digital Photographs from Unmanned Aircraft for Crop Monitoring", Remote Sens., 2010, 2, pp. 290-305.

Jurdak, et al., "Autonomous surveillance for biosecurity", 33-4, Apr. 1, 2015.

International Search Report for PCT No. PCT/IL2020/050029 dated Feb. 19, 2020.

Office Action for U.S. Appl. No. 16/242,012 dated Aug. 8, 2020.

Gonzalez-de-Santos, Pablo, et al. "Fleets of robots for environmentally-safe pest control in agriculture." *Precision Agriculture* 18 (2017): 574-614.

* cited by examiner

AUTONOMOUS CROP MONITORING SYSTEM AND METHOD

CROSS-REFERENCE TO RELATED APPLICATIONS

This application is a US National Phase of PCT International Patent Application No. PCT/IL2020/050029, International Filing Date Jan. 8, 2020, claiming the benefit of U.S. patent application Ser. No. 16/242,012 filed Jan. 8, 2019, which is hereby incorporated by reference.

FIELD OF THE INVENTION

The present invention relates to crop monitoring. More particularly, the present invention relates to a system and method for autonomous crop monitoring.

BACKGROUND OF THE INVENTION

Control of pests and diseases in crops is an important part of agriculture, as well as a large expense. About 25 years ago, with the increased awareness of the need to reduce the use of pesticides, and with adoption of efficient integrated pest management (IPM) practices, crop growers worldwide began to adopt methods based on human inspectors or scouts who examine crops by eye to detect signs of infestation. The amount, type, and frequency of treatment may be determined in accordance with the detected signs. A disadvantage of this system is that since the human scouts typically are on foot, only a small part, e.g., 5% at most, of a field is sampled. Treatment is based on the assumption that an infestation in part of the field is likely present in the entire field.

SUMMARY OF THE INVENTION

There is thus provided, in accordance with an embodiment of the present invention, a system for autonomous crop monitoring. The system includes a mobile platform having one or a plurality of imaging devices configured to autonomously travel a path to scan a plurality of inspection regions in a field of crop and obtain images of the inspection regions and a processor configured to analyze the acquired images to detect an agricultural condition that requires attention (ACRA) and determine the location of that ACRA.

In some embodiments of the present invention, said ACRA is selected from the group consisting of infestation, disease, pests, weather conditions, weather inflicted damages, pesticides coverage, fertilizer coverage, crop irregularities, soil irregularities.

In some embodiments of the present invention, the mobile platform comprises an unmanned aerial vehicle (UAV).

In some embodiments of the present invention, the UAV is configured to fly over one or more regions of the field at a height in the range of up to 2 meters above tops of the crop.

In some embodiments of the present invention, the UAV is configured to fly over one or more regions of the field at a height in a range of 0.5 to 2 meters above tops of the crop.

In some embodiments of the present invention, the mobile platform comprises a terrestrial platform.

In some embodiments of the present invention, the system further includes a leaf bending mechanism configured to cause bending of leaves of a crop plant in the field when an image of the crop plant is being acquired by the imaging device.

In some embodiments of the present invention, the mobile platform comprises a UAV and the leaf bending mechanism comprises one or more rotors of the UAV. Wherein a controller of the UAV is configured to cause the UAV to fly over the field at an altitude that is sufficiently low above the crop plant such that a downwash from said one or more rotors is sufficiently strong to cause bending of the leaves and to concurrently operate said one or a plurality of imaging devices to acquire one or more images of the crop plant.

In some embodiments of the present invention, the mobile platform comprises a terrestrial platform and wherein the leaf bending mechanism comprises a blower.

In some embodiments of the present invention, the system includes a controller configured to cause the mobile platform to travel along a predetermined scan path.

In some embodiments of the present invention, the controller is configured to operate said one or a plurality of imaging devices to acquire images along the predetermined scan path.

In some embodiments of the present invention, the scan flight path comprises a raster pattern over the field.

In some embodiments of the present invention, the scan flight path comprises flying to one or a plurality of inspection regions of the field, and flying over each of said one or a plurality of inspection regions in a predetermined flight pattern.

In some embodiments of the present invention, the predetermined flight pattern is selected from the group of flight patterns consisting of circle, oval, spiral and zigzag patterns.

In some embodiments of the present invention, the system includes a dispenser configured to dispense a treatment substance.

In some embodiments of the present invention, the system further includes a controller configured to autonomously analyze images that are acquired by said one or a plurality of imaging devices to detect ACRA in a region of the field, and to cause the dispenser to dispense the treatment substance on that region of the field.

In some embodiments of the present invention, the system includes an illumination source to illuminate a field of view of the imaging device.

In some embodiments of the present invention, there is provided a method for autonomous crop monitoring. The method includes providing a crop monitoring system comprising a mobile platform having one or a plurality of imaging devices configured to autonomously travel a path to scan a plurality of inspection regions in a field of the crop and obtain images of the inspection regions and a processor configured to analyze the acquired images to detect an agricultural condition that requires attention (ACRA) and determine the location of that AC; planning a path across a field of crop plants on the basis of a calculation of a likelihood of detection of agricultural condition requiring attention (ACRA) in one or more regions of the field; causing the mobile platform to travel along the planned path; operating said one or a plurality of imaging devices of the system to acquire images of the crop plants as the mobile platform travels along the planned path; and using a processor, analyzing the acquired images to detect ACRA and determine the location of that ACRA.

In some embodiments of the present invention, the mobile platform comprises a UAV, and wherein causing the mobile platform to travel along the planned path comprises causing the UAV to fly at an altitude that is sufficiently close to tops of the crop plants such that a downwash of a rotor of the UAV bends leaves of the crop plants.

In some embodiments of the present invention, the operating of said one or a plurality of imaging devices comprises acquiring images of higher resolution or at a higher density in a region of the field that is calculated by a controller to have a greater likelihood of ACRA than other regions of the field.

In some embodiments of the present invention, the size of a region of increased likelihood of ACRA about a location of a previously detected ACRA increases with increased precipitation since an estimated onset of the detected ACRA.

In some embodiments of the present invention, a shape of a region of increased likelihood of ACRA about a location of a previously detected infestation is elongated in direction of prevailing winds since an estimated onset of the detected infestation.

In some embodiments of the present invention, the mobile platform comprises a UAV.

In some embodiments of the present invention, the calculated path comprises a flight path in a predetermined flight pattern over one or a plurality of inspection region of the field.

In some embodiments of the present invention, the predetermined flight pattern is selected from the group of flight patterns consisting of circle, oval, spiral and zigzag patterns.

In some embodiments of the present invention, the method further includes analyzing the images that are acquired by said one or a plurality of imaging devices to count rows of crop plants, to identify a row in which the infestation was detected, and to measure a displacement along that row to identify a position of the location along that row.

In some embodiments of the present invention, the method includes optimizing image acquisition of the crop monitoring system using the equation $$\text{Total}(P(n)) = AI_{ac} * \sum_{k=1}^{n} \left( P_k * \left( \prod_{k=1}^{n-1} (1 - P_k)^{k-1} \right) \right)$$

where n is the number of acquired images required for a given probability level of detecting ACRA, k is the serial number of a current image obtained, $AI_{ac}$ is the accuracy level of an AI engine used, and $P_k$ is the probability to detect ACRA in the current image.

In some embodiments of the present invention, the method further includes optimizing image acquisition of the crop monitoring system using the equation:

$$\text{Total}(P(n))_{improved} = 1 - \left( \prod_{i=1}^{j} (1 - \text{Total}(P(n))) \right)$$

where i is the serial number of an image of a series of images of a same field cell of the field, and j is the total number of acquired images of that same field cell.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, a system is configured to autonomously scan and inspect crops in a field for signs of infestation, disease, pests, weather conditions, weather inflicted damages, pesticides coverage, fertilizer coverage, crop irregularities, soil irregularities, etc.—hereinafter generally referred to as "agricultural conditions requiring attention" (ACRA in short). The crop monitoring system is configured to identify, indicate a location and indicate a discovered condition of the ACRA, and in some embodiments of the invention is configured to autonomously return to the indicated location for a follow-up inspection.

In some embodiments of the present invention, the crop monitoring system includes one or more imaging devices (hereinafter—imaging devices) that are mounted on a mobile platform. The mobile platform may be dedicated to the crop monitoring system, or may be a mobile platform on which one or more components of the crop monitoring system are mounted. The mobile platform is capable of transporting the imaging devices of the crop monitoring system so as to enable imaging of any part of the field along a predetermined path or paths. For example, the mobile platform may include an unmanned aerial vehicle (UAV) or a terrestrial platform. For example, a UAV may be selected form a wide range of commercially available drones, such as, DJI Phantom™, DJI Mavic™, and drones manufactured by other vendors. A terrestrial platform may include a terrestrial vehicle (e.g., an autonomous or human operated tractor or other self-propelled or towed agricultural vehicle or equipment, cart, or other vehicle), an irrigation machine (e.g., center pivot irrigation machine, or linear move irrigation machine), a boat, or another terrestrial platform. In some embodiments of the present invention one or more imaging devices may be positioned at a fixed, stationary, location, for example attached to a pole, to a wall, to natural or artificial structure, or directly to the ground. In some embodiments of the invention, such stationary locations may include, for example, places in a field prone to pests, infection or other malicious conditions, like a muddled area, a place of irregular topology (e.g., a crack in the ground), or other such locations that are identified as susceptible to problems, e.g., biological or chemical infection or contamination or any other ACRA).

Imaging devices of the crop monitoring system may include one or more cameras, or other imaging devices, that are configured to acquire images of crops in the field. Typically, the images of crop plants that are acquired may be of different resolutions. For example, resolution may be adjusted by adjusting a zoom control (e.g., optical zoom or electronic zoom) of the imaging device, or by changing a distance between the imaging device and the crop plants being imaged (e.g., by changing an altitude of flight of a UAV, or adjusting the position of a mount of the imaging device on a terrestrial platform).

As used herein, the term "field" or "crop field" may refer to an entire agricultural tract of land that is defined by clear borders (e.g., that divide a field from abutting fields or regions of land). In some cases, the term "field" may refer to a part of such a tract that is treated by the crop monitoring system in manner that is different from another part of the field. For example, part of such a tract may be planted with one type of crop, while other parts are planted with a different crop. In this case, each such part may be referred to herein as a field.

An imaging device may be configured to acquire images in a single spectral range (e.g., images in visible light, multi-spectral range, thermal range, red-green-blue—RGB, infrared—IR, near infrared—NIR, ultraviolet—UV, etc.), or in two or more different spectral ranges, either concurrently or successively. In some cases, two or more imaging devices may be configured to acquired images in different spectral ranges. Images may be acquired as continuous video or as sequence of individual images acquired at intervals such that images of all parts of the field along a path of the mobile platform are imaged.

The imaging devices may be fixed on the mobile platform, or may be movable. For example, when mounted on a small UAV (e.g., a UAV that may be lifted by a single hand, or by one person, e.g., a quadcopter UAV), the position of an imaging device is typically fixed on the UAV. In some cases, the imaging device may be gimballed to enable pan and tilt adjustment, and may be provided with a lens having an adjustable zoom or focus. In some embodiments of the invention, the imaging devices may be stationary.

When mounted on a terrestrial vehicle, the nature of the mounting (e.g., fixed or movable) may be dependent on the type or size of vehicle, or its intended use. For example, when movement of the vehicle is limited to a particular path, e.g., between crop rows, the imaging device may be rotatable or translatable relative to the vehicle (e.g., along a boom that extends laterally from the vehicle, or on boom, e.g., a telescoping boom, of adjustable length). If the vehicle may be maneuvered to any position within the field (e.g., where a chassis of the vehicle is elevated above the crop plants), the imaging device may be fixed to a particular part of the vehicle.

When mounted on an irrigation machine, one or a plurality of imaging devices, typically gimballed or otherwise rotatable, may be fixed to different locations on a pipeline or support structure of the irrigation machine. In some cases, the imaging device may be mounted on a track, line, or other structure along which the imaging device may be translated (e.g., to different radial distances from a central pivot, or to different lateral positions perpendicular to a direction of motion of a linear move irrigation machine). The position on the imaging device on the irrigation machine may be selected to enable a clear view of the crop plants in the field, e.g., ahead of (or behind) drops or mist that are released from sprinklers of the irrigation machine. For example, the imaging devices may be mounted on arms or other structure that extends forward in the direction of motion of the irrigation machine.

In some cases, the crop monitoring system may include one or more sources of illumination. For example, an artificial illumination source may be utilized when ambient illumination is inadequate for effective scanimage acquisition, or when illumination in a particular spectral band is required.

Analysis of the acquired images may detect one or more signs of ACRA. Analysis of the images may also enable determination of an exact location the crop monitoring system when an image was acquired, e.g., relative to a fixed point in the field. For example, a UAV-based system may be configured to count rows that are crossed to determine a crop row in which an image was acquired. Analysis of images that are acquired of the ground and knowledge of a time at which each image (or video frame) was acquired may be analyzed to yield a position along a crop row.

The crop monitoring system may include capability of turning or bending leaves of a crop plant, e.g., to acquire images of an underside of a leaf or a stalk of a crop plant. For example, when the mobile platform of the crop monitoring system comprises a UAV, the crop monitoring system may be configured such that the UAV flies close to the tops of the crop plants. The distance between rotors of the UAV and the leaves, at least near the top of a crop plant, may be sufficiently small such the downwash from the rotors turns at least some of the leaves. For example, for a typical small UAV, e.g., with a weight of about one kilogram, and with four rotors, each with a diameter of about 25 cm, a height above the tops of the crop plants that provides sufficient downwash for leaf turning may be about two meters or less, in some embodiments between 0.5-2 meters over the crop tops, and in some embodiments even closer to the crop tops. The height for providing leaf downwash may depend on such factors as size, rotation velocity, and number of rotors, type of plants, current wind conditions, or other factors. When the mobile platform of the crop monitoring system includes a terrestrial platform such as a terrestrial vehicle or irrigation machine, a fan, blower, air or gas jet, rod, or other structure may extend from the terrestrial platform toward crop plants that are to be imaged so as to bend at least some leaves of the crop plants.

A controller of the crop monitoring system includes one or more processors that may be configured to operate the crop monitoring system in accordance with one or more parameters. These parameters may be based on one or more of data that was acquired by the crop monitoring system itself, user input, information that is acquired (either autonomously or in response to a user command) from one or more outside resources with which the crop monitoring system may communicate, or that is otherwise acquired. The processors may be included within the crop monitoring system (e.g., mounted on the mobile platform), on a stationary unit of the crop monitoring system (e.g., in or near the field being scanned), or at a remote station, e.g., that serves a plurality of crop inspection systems.

For example, the crop monitoring system may include one or more navigation aids (e.g., receiver of a Global Positioning System (GPS) signal or other navigation signal, inertial scan unit (IMU), altimeter, radar, lidar, rangefinder, compass, or other navigation aids), meteorological or other environmental sensors (e.g., for temperature, humidity, wind speed or direction, barometric pressure, precipitation, insolation, concentrations of particulate or other pollutants or atmospheric components, or other meteorological or environmental conditions, such as heavy rain, frost, hale), imaging devices configured to identify markers, biomarkers (e.g., indicative of the spread of a new invasive species in a given area, in an immediate or distant environment, spread of disease and/or other biomarkers in animals, plant species, crops, and other indications relating to the current condition of the crop, the field, or other entities, or other sensor systems or components. The controller of the crop monitoring system may utilize data from one or more of the sensors in planning an image acquisition path to scan a field. The controller may include, or may communicate with, a clock that may indicate a current date and time of day. The controller may be configured to utilize time and geographical data to calculate a current position of the sun.

The controller may be configured to utilize data related to previous scans that were made by the crop monitoring system on a field. For example, the crop monitoring system may be configured to recall locations of a field where follow-up scans are indicated (e.g., where indications of infestation or other ACRA had been noted, or where results of a scan were inconclusive, where a treatment had been applied, where an appropriate period of time has elapsed from a previous scan, or other circumstances that may indicated that a follow-up scan is called for). The controller may utilize data that is entered by a user that is related to a scan. For example, a user may enter information related to boundaries and topography of a field, locations of various features of a field (e.g., barriers, components of an irrigation system, types of crops, previously applied treatments, or other features of, or information related to, a field).

The controller may be configured to communicate with one or more remote services or sources of information. For example, such remote services may include a meteorological service, a database of locations known present or recent infestations in the vicinity of the field, a database of geographical information (e.g., usage of land in the vicinity of the field, presence of human or animal populations that may restrict treatment, or other geographical information), or other providers of relevant information. The controller may communicate with one or more internet-of-things (IOT) sensors, a remote meteorological station, or other remote sensors.

The controller may utilize various parameters and data from one or more sources to plan a path for imaging the field. For example, a path may be determined on the basis of information that effects data acquisition (e.g., illumination, interference from fog, haze, or precipitation, or other factors), navigation of the mobile platform (e.g., wind conditions or precipitation, temperature, or other conditions), likelihood of infestation (e.g., based on infestations in the area, past infestations, wind, meteorological conditions that affect infestation, or other conditions), or other considerations.

For example, a path, in particular a flight path of a UAV, may be planned such that the fields of view of the acquired images completely cover the field. Thus, the field of view of each acquired image is contiguous (e.g., abuts or at least partially overlaps) with the field of view of at least one other image. For example, when a flight path includes a raster pattern, the lateral displacement between successive parallel legs of the raster pattern are selected such that the fields of view of images acquired in those successive legs are laterally contiguous (e.g., the images along one leg are contiguous with images of the adjacent leg). If the field of view is decreased, e.g., as a result of increasing resolution, the spacing between different legs of a flight path may be decreased accordingly.

Alternatively or in addition, the fields of view of the acquired images over parts of the field may not be contiguous. For example, separations between fields of view may be such that representative images of the field are acquired at a predetermined density. The predetermined density may be selected so as to provide sampling such that a distance between fields of view of successively acquired images or between legs of path does not exceed a predetermined distance.

For example, the controller may control the crop monitoring system to closely examine at higher resolution, with greater density (e.g., decreased distance between fields of view of successively acquired images), or at higher resolution and greater density, a region of the field, or the entire field, when infection is determined to be likely on the basis of data that is available to the crop monitoring system. For example, increase likelihood of infestation may be calculated for a region of a field where preventative treatment is not possible or forbidden (e.g., a region of a field near populated residences or offices, or the presence of buildings, power lines, towers, or other structure that may interfere with aerial spraying or crop dusting), a region of the field that are especially moist (e.g., near an irrigation machine pivot) or where water is likely to accumulate (e.g., a depression), a region that includes vegetation other than the crop plant (e.g., remainders of previous crops, weeds, seeds that were carried by wind or fauna, other varieties of the crop plant), a region that is downwind of infested regions of the field or of nearby (e.g., up to a distance of one kilometer) fields, or that otherwise has an increased likelihood of infestation. A pattern of expected spread of infestation from an infested region may depend on wind conditions, precipitation, humidity, or other factors. Close examination may include one or more of increased coverage density (e.g., paths over the region that abut or partially overlap), slower travel over those regions (e.g., to acquire a greater density of images of those regions of the field), increased resolution or image acquisition rate, increased frequency of repeat examination of those regions, application of a wider variety of imaging (e.g., in different spectral bands) or image processing techniques, or other techniques that increase the likelihood of detection of any infestation.

In the absence of any factors related to increased likelihood of infestation, the mobile platform may cause the crop monitoring system to travel in a basic inspection pattern. For example, the crop monitoring system (e.g., that is mounted on a UAV or terrestrial vehicle) may across the entire area of the field in a raster pattern or spiral pattern while acquiring images at a lower resolution or at a lower density. At selected inspection regions that are distributed throughout the area of the field, the crop monitoring system may be configured to inspect region at a higher resolution or higher density in a denser pattern. The number of inspection regions may be selected to provide coverage of the field that is sufficiently dense so as to enable detection of an infestation with a satisfactory likelihood. For example, in each of the inspection regions, the mobile platform (e.g., a UAV) may be operated to cover the region in a dense zigzag, spiral, or other pattern. For example, each straight segment of a zigzag pattern, or each complete circuit (e.g., return to a starting azimuth relative to a center) of a spiral pattern, may be located such that each field of view of an imaging device of the crop monitoring system during that leg or circuit is contiguous (e.g., closely abutted or partially overlapped by) the field of view of an image acquired during the following segment or circuit. In this manner, the field of view may cover the entire area of each inspection region.

Segmentation of the area of the field into segments, some of which may be selected to be inspection regions, may depend on several factors such as density of crop plants, meteorological conditions, identified susceptible regions of the field, previous history of usage and infestations, or other factors. A segmentation may be fixed for a field, or may change from inspection to inspection, or, in some cases, during the course of an inspection (e.g., dependent on inspection results and current conditions).

After an infestation has been detected, either before of after treatment, the UAV may fly in a follow-up inspection pattern. A follow-up inspection pattern may be configured to closely examine regions of the field that are liable to have been infested by spread of the originally detected infestation.

For example, the follow-up inspection pattern may be planned on the basis of recent meteorological conditions. Typically, a distance to which an infestation is capable of spreading increases as a function of increased precipitation (e.g., rain). Similarly, a distance to which an infestation is expected to spread typically increases with wind velocity and duration in each direction. A follow-up inspection region typically includes, and extends outward from, a location where the infestation was previously detected. A size (e.g., radius, major and minor axis of an ellipse, sides of a rectangle or trapezoid, or other representative dimension) of the follow-up inspection region may increase as a function of increasing recent precipitation. For example, recent precipitation may have fallen during an appropriate period preceding detection of the infestation (e.g., during which the infestation may have spread without detection), and during a period since detection of the infestation. Similarly, a shape of the follow-up inspection region (e.g., eccentricity of an elliptical region) may be elongated along a direction of recent winds, and increasing as a function of velocity or frequency of those winds. For example, a follow-up inspection region may be inspected in a raster pattern, a spiral pattern, a zigzag pattern, or otherwise.

In some cases, inspection of a field may combine follow-up inspection or other enhanced inspection in appropriate areas, as well as basic inspection of the remainder of the field.

A crop monitoring system as described herein may be advantageous over other types of systems or methods. For example, human scouts typically inspect only a small sample of a field, typically at an edge of the field. Therefore, when infestation is discovered, in order to ensure that all affected parts of the field are treated, the treatment would be applied to the entire field. On the other hand, use of a crop monitoring system as described herein may enable inspection of all parts of the field, or sampling across the entire area of the field, and timely reinspection of those parts of the field that are determined to be susceptible to a detected infestation. Frequent follow-up inspection would also be possible.

A crop monitoring system as described herein is configured to enable enhanced inspection (e.g., along a densely arranged inspection route) that is selected in accordance with criteria that are indicative of where infestation is likely to be found. Such directed inspection is likely to yield more accurate results than random sampling of locations in the field, and quicker and less costly results than comprehensive inspection of the entire field.

In some cases, e.g., where the crop monitoring system is mounted on a terrestrial vehicle or on an irrigation machine (or on a large UAV), the crop monitoring system may be configured to immediately apply a treatment to a region of a field in which infestation has been detected. For example, an irrigation machine may be equipped with one or more dispensers that are controllable to dispense a pesticide or other treatment substance at specific locations of a field. For example, the treatment substance may be added to irrigation water that is to irrigate an infested region, or to a region to which infestation is likely to spread. Similarly, a terrestrial vehicle may include a dispenser, or may tow a dispenser, for dispensing the treatment substance. For example, the imaging device of the crop monitoring system may be mounted at the front of the terrestrial vehicle and a substance dispenser may be located further back on the terrestrial vehicle. In this case, movement of the vehicle may allow for sufficient time between imaging a crop plant and being in position to dispense a substance on that crop plant to enable analysis to determine whether or not dispensing of the substance on that plant is indicated.

Figure 1:
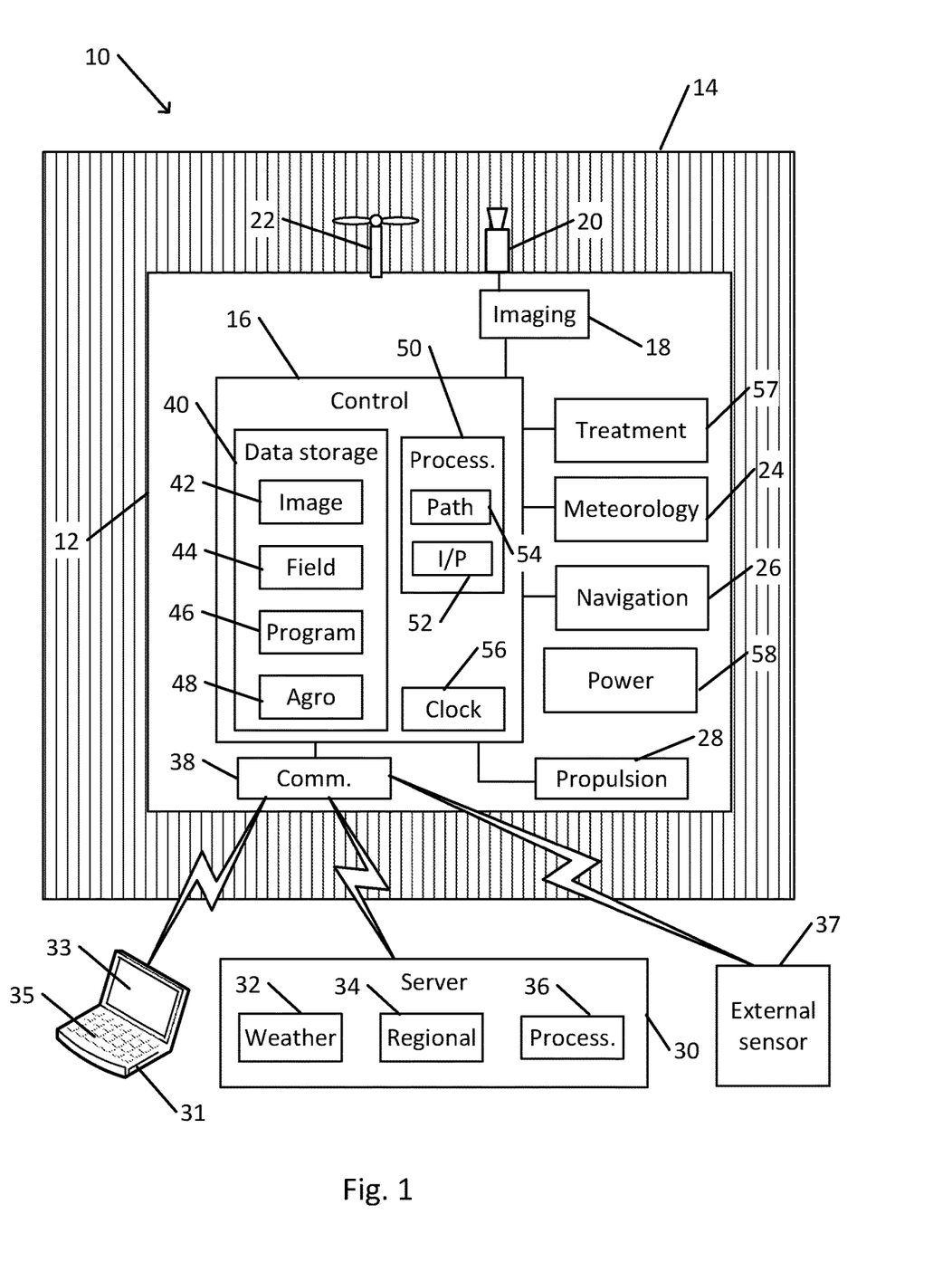
FIG. 1 is a schematic block diagram of a crop monitoring system, in accordance with an embodiment of the present invention.

FIG. 1 is a schematic block diagram of a crop monitoring system, in accordance with an embodiment of the present invention.

Crop monitoring system 10 includes mobile platform 12. For example, mobile platform 12 may include a UAV, a terrestrial vehicle (e.g., manned, remotely controlled, or autonomous), an irrigation machine (e.g., center pivot or linear move), or another mobile platform. Some or all components of crop monitoring system 10 that are mounted on mobile platform 12 or otherwise incorporated into mobile platform 12 may include components that are typically incorporated into, mounted on, enclosed within, or that are otherwise part of a particular mobile platform 12 (e.g., when used for purposes other than crop monitoring), or may be incorporated into mobile platform 12 for adaptation for operation as part of crop monitoring system 10.

Crop monitoring system 10 is configured to operate in a crop field 14. For example, crop field 14 may include a region in which one or more types of crop plants (which may include trees) are planted. Typically, the crop plants in crop field 14 are arranged in straight or curved rows which are separated from one another by spaces. The vicinity of crop field 14 may include one or more neighboring fields and other topographical or manmade structures at varying distances from crop field 14.

Controller 16 of crop monitoring system 10 may be configured to control one or more systems or components of crop monitoring system 10. Controller 16 may include one or more control units. The control units of controller 16 may be located at a single location (e.g., on board mobile platform 12, on a remote control unit for operation of crop monitoring system 10, or elsewhere), or may include intercommunication units that are at several mutually remote locations. The control units of controller 16 may include one or more hardware or software modules that may interface with various components of crop monitoring system 10.

Controller 16 may include a processor 50. Processor 50 may include one or more processing units. A processing unit of processor 50 may include a general purpose computer, or a specialized processing device. Processing units of processor 50 may be located at a single location (e.g., on a single circuit board or enclosed in a single housing), or may be mutually remote from one another.

Controller 16 may include data storage 40. Data storage 40 may include one or more volatile or nonvolatile, fixed or removable, local or remote, memory or data storage devices. For example, data storage 40 may be utilized to store programmed instructions 46 for operation of processor 50, parameters and data for utilization by controller 16 in determining control of crop monitoring system 10, and results of operation of crop monitoring system 10.

Data storage 40 may be utilized to store information related to operation of crop monitoring system 10.

For example, data storage 40 may be utilized to store image data 42 that is acquired by imaging device 20. Image data 42 may include information related to acquisition of a stored image. Such information may include a time stamp (e.g., based on data provided by controller clock 56), data related to a location at which the image was acquired, or other information.

Data storage 40 may be utilized to store information that was provided by a user (e.g., via communication with user device 31), by a remotely stored database (e.g., via communication with remote server 30), or otherwise. Such information may include field data 44 related to crop field 14 (e.g., a location, boundaries, topography, or layout of crop field 14, structures or obstacles in or near crop field 14, type of crop planted, field history including time since planting, previous crops, treatments applied, irrigation, or other information). The information may include agronomic data 48, including, e.g., locations and types of infestations in neighboring fields, or other relevant information.

Controller 16 may be provided with a communications module 38 to enable controller 16 to communicate with one or more external devices via a wired or wireless communications channel. For example, communications module 38 may include one or more antennas, sockets, connectors, or other components that enable communication with an external device. A communications channel may include a direct wired or wireless connection, or may include communications via a network such as the internet, a mobile telephone network, or another local, regional, or global network. An external device with which controller 16 may communicate via communications module 38 may include a remote server 30, a user device 31, one or more external sensors 37 (e.g., a remote meteorological station, navigation beacon, radar or lidar transceiver, or another external sensor), another crop monitoring system 10, or another external device.

Remote server 30 may include a server of one or more remotely located services. In some cases, remote server 30 may include a service that provides one or more of processing services, databases, or other information to one or more crop monitoring systems 10. For example, in some cases, a controller 16 may be configured to transmit acquired images or other data to remote server 30 for processing by a processing module 36 of remote server 30 (e.g., to provide greater processing capability than may be provided by some types of processor 50). In some cases, remote server 30 may include a server of one or more information services, e.g., that provide weather services 32 (e.g., records of past weather conditions or forecasts of expected weather conditions), or regional information 34 (e.g., boundaries or locations of crop field 14 or of neighboring fields, history or infestations or treatments in crop field 14 or in neighboring fields, topography and structures in crop field 14 or in the region surrounding crop field 14, or other regional information for use by processor 50 or processing module 36).

A user device 31 may include a fixed or mobile computer, a tablet computer, smartphone, or other device that may enable a user to interact with crop monitoring system 10. For example, user device 31 may include one or more output devices 33 (e.g., display screen or other output device) that may enable a user to monitor operation or a status of crop monitoring system 10, review results of scans by crop monitoring system 10, or other information. User device 31 may include one or more input devices 35 (e.g., touchscreen, keyboard or keypad, microphone, controls, or other types of input devices) to enable a user to input commands, programming instructions, data or other input to crop monitoring system 10, control operation (e.g., manual override or other control) of crop monitoring system 10, or other user input.

Controller 16 of crop monitoring system 10 may communicate with one or more sensor units of crop monitoring system 10. For example, sensor units may include meteorology unit 24, navigation unit 26, or other sensor units.

Meteorology unit 24 may include one or more sensors for sensing a meteorology-related property at, or in the immediate vicinity of, crop monitoring system 10. For example, meteorology unit 24 may include (e.g., depending on a size or type of mobile platform 12) a thermometer, humidity sensor, wind vane, anemometer, insolation meter, precipitation gauge, or other sensor. In some cases, controller 16 may communicate via communications module 38 with one or more meteorological stations that are located near (e.g., within or near a boundary of) crop field 14. Such a meteorological station may include, for example, one or more meteorological sensors, which may include sensors that are too heavy or bulky to be included in meteorology unit 24, or that are designed to operate from a fixed location.

Navigation unit 26 may include one or more sensors or units that enable determination of a position, orientation, or speed or direction of motion of mobile platform 12. For example, navigation unit 26 may include one or more of a Global Positioning System (GPS) receiver, a compass, IMU, speedometer or airspeed meter, altimeter, rangefinder, tilt meter, gyroscope, or other sensor or device for assisting in navigation. In some cases, navigation unit 26 may interact with or otherwise utilize one or more external navigation aids, such as a position marker or beacon at a known location, to assist in navigation.

Controller 16 may control operation of one or more systems of units of crop monitoring system 10, e.g., based on processing or data acquired via one or more of communications module 38, data storage 40, meteorology unit 24, navigation unit 26, or other units or systems.

For example, processor 50 may execute path calculation module 54 to calculate a path for travel by mobile platform 12.

Execution of path calculation module 54 may select a flight path for a mobile platform 12 in the form of a UAV on the basis of one or more criteria. For example, for calculation of a flight path in a part of crop field 14 that was not previously determined to have a greater likelihood of infestation than other parts of crop field 14, the calculated path may include a raster pattern (e.g., back and forth along laterally displaced mutually parallel straight segments) over the entire area of crop field 14, and dense coverage of previously selected inspection regions within crop field 14. As used herein, dense coverage refers to a path in which the field of view of each acquired image of the inspection region is contiguous with (e.g., abuts, or is partially overlapped by) the field of view or one or more other images within the inspection region, despite the increased resolution and resulting reduced field of view. For example, the flight path within the inspection region may include a dense zigzag pattern, or, in some cases, a dense spiral or other pattern. If infestation has been previously detected in crop field 14 or in a neighboring field, execution of path calculation module 54 may calculate a flight path that includes dense flight path over those parts of crop field 14 having an increased likelihood of infestation. For example, the calculation of the flight path may include calculation of an estimated onset of the infestation (e.g., based on a type of infestation, a typical incubation period, a period of time between inspections, meteorological conditions, or other factors). A likelihood of infestation in each part of crop field 14 may depend on a distance from the detected infestation, precipitation and wind conditions since the estimated onset, or other conditions.

When mobile platform 12 is in the form of a terrestrial platform, motion of mobile platform 12 may be limited to a fixed path. For example, a terrestrial vehicle may be constricted to motion along within a space between adjacent crop rows. An irrigation machine typically is limited to travel along a fixed linear or circular path. In such cases, path calculation module 54 may not be executed. In some cases, e.g., when a limited number of imaging devices 20 are mounted on rotatable or translatable mounts (e.g., on forward extending or laterally extending arms or booms), path calculation module 54 may operate imager control module 18 to scan fields of view of one or more imaging devices 20 in order to increase likelihood of detection of any infestation in crop field 14. In some cases, motion of a terrestrial mobile platform 12 may be sufficiently slow to enable dense coverage of the entire area of crop field 14.

Controller 16 may then operate propulsion unit 28 of crop monitoring system 10, e.g., in coordination with data from navigation unit 26, to cause mobile platform 12 to travel along the calculated path. Depending on the type of mobile platform 12, propulsion unit 28 may include a propeller, a motorized wheel, a steering mechanism (e.g., propeller tilting mechanism, wheel turning mechanism, rudder or airfoil, or other steering mechanism), a transmission, or other suitable components.

Controller 16 may be configured to control operation of imaging device 20. Imaging device 20 may include one or more cameras or other imaging devices (e.g., IR imaging devices, portable cameras, smartphones, etc.). Controller 16 may send commands to imager control module 18 to control operation of imaging device 20. For example, control of operation of imaging device 20 may include control of acquisition of images, transfer of images from imaging device 20 to data storage 40 as image data 42, control of an aiming mechanism (e.g., gimballed pan/tilt mechanism, or otherwise), of a focusing or zoom mechanism, or other operation.

Controller 16 may be configured to control operation of leaf bending mechanism 22. In some cases, leaf bending mechanism 22 may be an active device, such as a fan, blower, air or gas jet, rotor of a UAV, or other mechanism for creating air movement that may bend, turn, or rotate leaves of a crop plant. Alternatively or in addition, leaf bending mechanism 22 may include a component (e.g., bar, roller, or other mechanism), for mechanically turning or bending a leaf. In cases where leaf bending mechanism 22 operates independently of propulsion unit 28, leaf bending mechanism 22 may operate continuously (e.g., during operation of crop monitoring system 10 or when imaging device 20 is being operated to acquire images), or may operate intermittently (e.g., when processing of image data indicates that leaf bending may be advantageous). When operation of leaf bending mechanism 22 is linked to operation of propulsion unit 28 (e.g., when leaf bending mechanism 22 includes downwash by a rotor of a UAV, or is otherwise coupled to a component of propulsion unit 28), leaf bending mechanism 22 may operate continuously whenever mobile platform 12 is in motion.

For example, bending one or more leaves of a crop plant may expose an underside of a leaf, or of a stem or stalk of the crop plant, to imaging device 20. Thus, an indication of infestation that is located on an underside of a leaf, or on a part of a crop plant that is ordinarily covered or blocked from view by leaves of the plant, may be visible in an image that is acquired by imaging device 20.

Image processing (I/P) module 52 may executed on processor 50 of controller 16. Execution of image processing module 52 may analyze images that are acquired by imaging device 20. Analysis of the images may identify any indications of one or more types of infestation or other ACRA. For example, one or more detected patterns of coloring (e.g., visible coloration or variation in other spectral ranges) on a leaf or stalk of a crop plant may be associated with one or more types of infestation or other ACRA.

In some cases, controller 16 may operate a treatment unit 57 of crop monitoring system 10. For example, treatment unit 57 (on a mobile platform 12 in the form of a terrestrial platform such a terrestrial vehicle or irrigation machine) may be configured to dispense a treatment substance (e.g., chemical or biological material) at one or more locations on crop field 14.

In some cases, controller 16 may be configured to decide autonomously when to operate treatment unit 57. For example, when image processing module 52 may detect an indication of infestation at a particular location of crop field 14, controller 16 may operate treatment unit 57 at that location. Typically, in a mobile platform 12 in the form of a terrestrial platform, imaging device 20 may be aimed at a part of crop field 14 that is ahead of, or at, a front end of mobile platform 12 (e.g., on an arm or boom that extends forward or laterally outward from mobile platform 12). On the other hand, on such a typical terrestrial mobile platform 12, treatment unit 57 may be located rearward from imaging device 20 (e.g., as part of the irrigation apparatus of an irrigation machine, or on an attachment that is attached to the rear of, or is towed by, a tractor or similar vehicle). Thus, sufficient time may elapse between imaging of an indication of infestation or other ACRA and application of a treatment to enable analysis of the images and an autonomous or assisted (e.g., by a user operating user device 31) decision whether or not to apply a treatment.

Power supply 58 for operation of components of crop monitoring system 10 that are mounted on mobile platform 12 may include one or more storage batteries, or other sources depending on a type of mobile platform 12. For example, power supply 58 a mobile platform 12 in the form of a UAV may include a rechargeable or replaceable storage battery, solar cells, or another source (e.g., a directed electromagnetic beam) of electrical power. A power supply 58 of a mobile platform 12 in the form of a terrestrial vehicle (e.g., tractor or other vehicle that is operated by an internal combustion engine) may include a storage battery that is continually recharged by operation of the vehicle engine. A power supply 58 for a mobile platform 12 in the form of an irrigation machine may include a power source for operation of the irrigation machine (e.g., a storage battery, solar panel, line voltage that is provided via a pivot, or another source of electrical power).

Figure 2A:
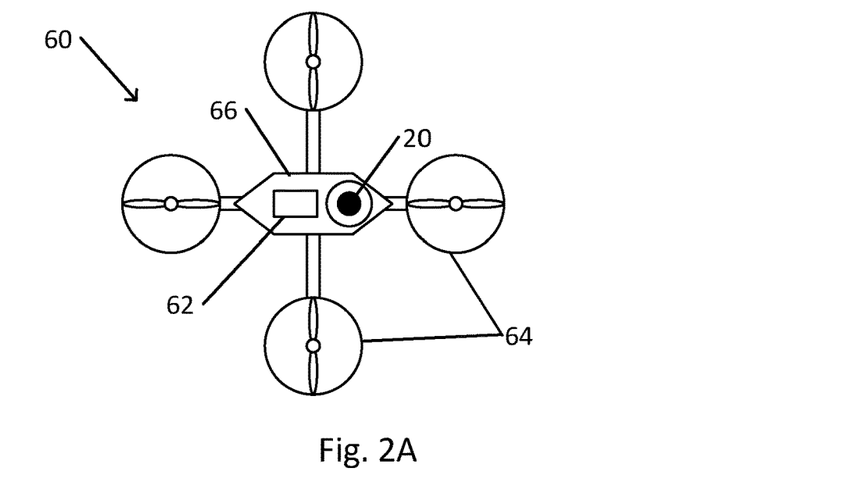
FIG. 2A schematically illustrates a crop monitoring system based on a mobile platform in the form of a UAV.

FIG. 2A schematically illustrates a crop monitoring system based on a mobile platform in the form of a UAV.

In the example, shown, UAV 60 is a quadcopter UAV having UAV body 66 and four rotors 64. Rotors 64 may be operated (e.g., by individually controlling the speed of rotation of each rotor 64) to control yaw, pitch, and roll, and thus thrust and lift of UAV 60. Other types of UAV may include other numbers of rotors, or fixed wings, propellers, and controllable flaps.

In the example, shown, a payload on UAV body 66 may be limited to camera 20 (which may be gimbal-mounted or otherwise have a controllable pan and tilt) and a built-in controller 62 (e.g., provided by a manufacturer of UAV 60). Controller 62 may include an IMU or other navigation components, a processor, and control of rotors 64. Therefore, any additional sensors or processing capability may be provided by communication, e.g., with a user device 31 or remote server 30 that is in communication with other sensors or devices. In other examples, a UAV may be configured to hold larger payloads.

Figure 2B:
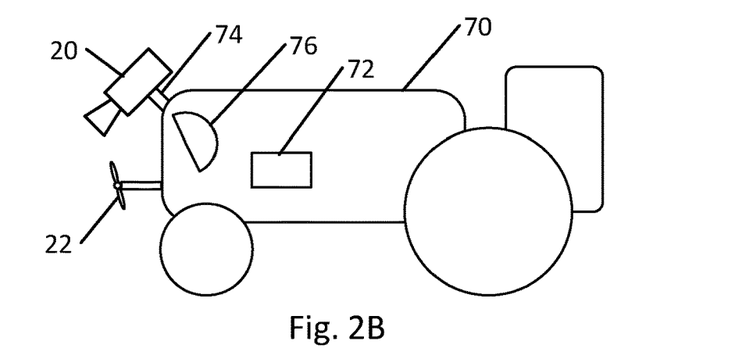
FIG. 2B schematically illustrates a crop monitoring system based on a mobile platform in the form of a terrestrial vehicle.

FIG. 2B schematically illustrates a crop monitoring system based on a mobile platform in the form of a terrestrial vehicle.

Terrestrial vehicle 70 may include one or more imaging devices 20. Typically, each imaging device 20 is mounted on an arm 74. Since travel of a typical terrestrial vehicle 70 is limited to spaces between adjacent crop rows (e.g., so as not to damage the crops), arm 74 may extend laterally (e.g., toward the right or left) of the direction of travel of terrestrial vehicle 70. In some cases, an illumination source 76 (e.g., a spotlight, or other light source) may be mounted on terrestrial vehicle 70 (or on another type of mobile platform 12) to illuminate a field of view of imaging device 20. Typically, illumination source 76 is shield so as to preventing light that is emitted by illumination source 76 from directly illuminating (and potentially blinding) imaging device 20.

A controller 72 may be located on terrestrial vehicle 70 or within a compartment of terrestrial vehicle 70.

One or more leaf bending mechanisms 22 may be located near (e.g., below) each imaging device 20. Leaf bending mechanism 22 may be operated to bend leaves on a crop plant that is being imaged by imaging device 20 to enable acquisition of images of an underside of leaves of the crop plant or a stalk of the crop plant.

Figure 2C:
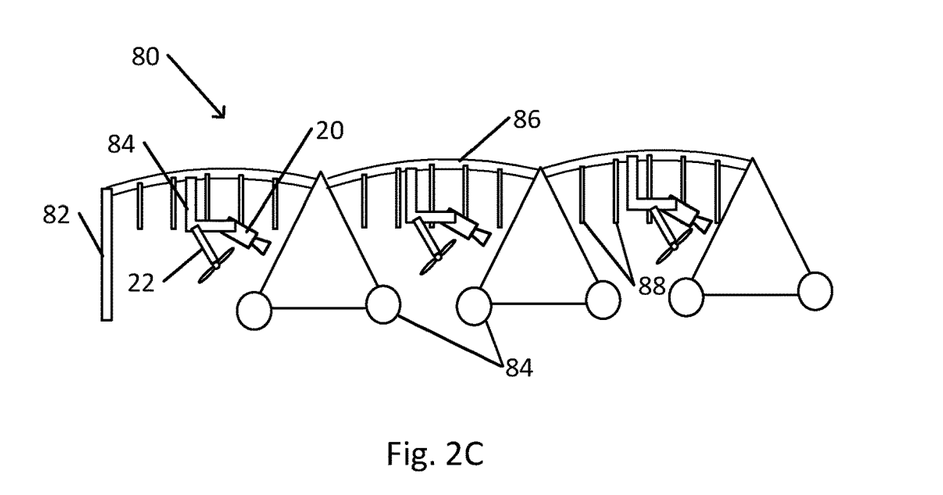
FIG. 2C schematically illustrates a crop monitoring system based on a mobile platform in the form of an irrigation machine.

FIG. 2C schematically illustrates a crop monitoring system based on a mobile platform in the form of an irrigation machine.

In the example shown, irrigation machine 80 is a central pivot irrigation machine that includes irrigation pipe 86 that extends radially from pivot 82. A plurality of irrigation nozzles 88 extend downward from irrigation pipe 86 along the length of irrigation pipe 86. Propulsion mechanism 84 (e.g., including a plurality of motorized or hydraulically operated wheels) may be operated to cause irrigation pipe 86 to rotate about pivot 82. Water that is fed into irrigation machine 80 via pivot 82 may be transported to irrigation nozzles 88 via irrigation pipe 86, where the water is directed downward as a spray or mist.

One or more imaging devices 20 are mounted to irrigation pipe 86 (or other structure of irrigation machine 80) via arms 84. Each arm 84 may be configured such that a line of sight between an imaging device 20 that is mounted to an arm 84 and a crop plant being imaged is not obscured by water that is being sprayed out of irrigation nozzles 88. In some cases, arm 84 may be configured to transport imaging device 20 along the length of (or parallel to) irrigation pipe 86.

Each imaging device 20 may be provided with a leaf bending mechanism 22 to bend leaves of crop plants being imaged by that imaging device 20.

Controller 16 of a crop monitoring system 10, e.g., whose mobile platform is in the form of a UAV 60, may be configured to execute a method for crop monitoring.

Figure 3A:
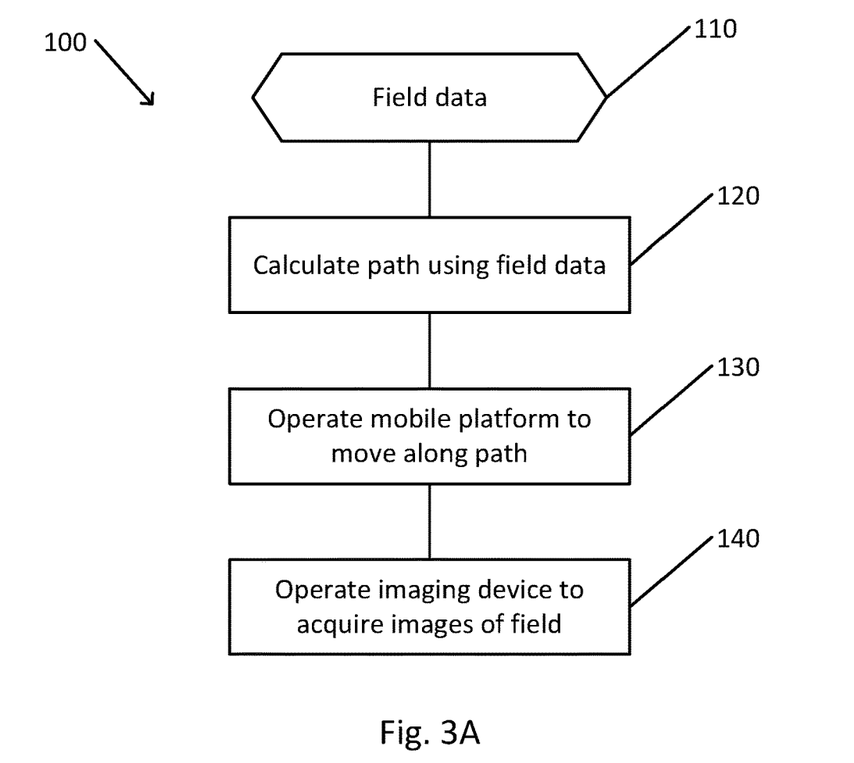
FIG. 3A is a flowchart depicting a method of autonomous crop monitoring by a crop monitoring system, in accordance with an embodiment of the present invention.

FIG. 3A is a flowchart depicting a method of autonomous crop monitoring by a crop monitoring system, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Crop monitoring method 100 may be executed by controller 16 of a crop monitoring system 10, e.g., of a crop monitoring system 10 whose mobile platform 12 includes a UAV 60. For example, crop monitoring method 100 may be executed prior to, and during, scanning of crop monitoring system 10 of a crop field 14. In some cases, e.g., depending on type of crop, stage of crop growth, conditions of d crop field 14, characteristics of mobile platform 12, crop monitoring method 100 may be executed for a crop monitoring system 10 that includes a mobile platform 12 that is not a UAV. In some cases, crop monitoring method 100 may be applied to movement (e.g., translation, rotation, or both) of one or more imaging devices 20 on mobile platform 12 as mobile platform 12 travels on a constrained path across crop field 14. Therefore, references to a UAV, flight path, flight, or similar terms with regard to execution of operations of crop monitoring method 100 should be understood as also applicable to those situations where mobile platform 12 is not a UAV or any other aerial platform.

Controller 16 may have access to data related to crop field 14 (block 110). For example, the data may include types of crops in crop field 14, topography of crop field 14, structures in or near crop field 14 that may affect a flight path of UAV 60, locations of previously detected infestations in crop field 14 or in a neighboring field (from which there is a significant likelihood, e.g., with a probability above a predetermined value, of spread of the infestation to crop field 14), current and recent (e.g., that are considered to have a significant effect, in accordance with predetermined criteria, on a likelihood of infestation of crop field 14) meteorological conditions, data related to previously applied treatments to crop field 14, characteristics and capabilities of UAV 60 (e.g., speed, altitude, or flight time limitations, maneuverability, or other characteristics), or other data. Some or all of the data may be stored in data storage 40, e.g., as field data 44, agronomic data 48, or otherwise. Alternatively or in addition, some or all of the data may be obtained via communications module 38 from one or more of remote server 30, external sensors 37, user device 31, or from elsewhere.

In some cases, data may include raw or processed images that may be acquired by other platforms. Such images may include, for example, aerial and satellite images, and may include multispectral, hyperspectral, infrared, visible, or other types of images.

Controller 16 (e.g., in accordance with programmed instructions 46) may plan a path of motion of mobile platform 12 over crop field 14 on the basis of the field data (block 120). For example, the planned path may be based on a calculation that utilizes information regarding any previously detected infestations in crop field 14 or in a neighboring field, and regarding conditions that may affect spread of the infestation.

For example, a basic flight path over a field where there are no indications of increased likelihood of infestation or other ACRA may include a flight path that is designed to cover all of crop field 14 (e.g., the entire set of acquired images covering all of crop field 14), while covering predetermined inspection regions of crop field 14 at a higher resolution (e.g., increased camera zoom or at lower altitude). Thus, in the inspection regions, the density of successive legs of the flight path may be more densely spaced than when covering regions of crop field 14 outside of the inspection regions.

As another example, a path over regions of crop field 14 that are within a region of crop field 14 having an increased likelihood (e.g., in accordance with predetermined criteria) of spreading of a previously detected infestation may be denser than a path over other regions of crop field 14. In other embodiments of the invention the crop monitoring system may fly from one inspection region to another and scan only these regions.

In some cases, may be configured to autonomously identify regions with increased likelihood of infestation, or other problematic regions, in images from other platforms.

As another example, a path may be designed to enable inspection (e.g., at greater density or resolution than other parts of crop field 14) of a part of a field where a treatment had previously been applied, e.g., in order to evaluate the efficacy of the treatment.

In some cases, a path may be designed to avoid blinding of imaging device 20 by sunlight or to avoid shading of a field of view by mobile platform 12. For example, a calculation may calculate the position of the sun and plan the path such that imaging device is not aimed into the sun, or that the field of view is in a direction that is not shaded by mobile platform 12. Alternatively or in addition to calculating a position of the sun, a sunlight or insolation sensor, e.g., of meteorology unit 24, may measure a current direction of the sun. An orientation of mobile platform 12, imaging device 20, or both may be adjusted to avoid blinding or shading by sunlight.

In some cases, controller 16 may be configured to, in addition to planning a path across crop filed 14, schedule a scan. In some cases, operation of crop monitoring system 10 at the scheduled time may be automatic. In some cases, operation of crop monitoring system 10 may be subject to confirmation by a user (e.g., depending on type of mobile platform 12, expense of operation of crop monitoring system 10, other scheduled activities in the vicinity of crop field 14, or other considerations). For example, on or after a day when winds were blowing from a direction of an infestation in a neighboring field, controller 16 may schedule a scan of crop field 14 at an earlier date than when such a scan would have been otherwise scheduled.

Controller 16 may operate propulsion unit 28 of mobile platform 12, e.g., UAV 60, to fly over, or otherwise travel over, crop field 14 along the planned path (block 130). During operation of mobile platform 12, controller 16 may utilize information received from navigation unit 26 in operating mobile platform 12 to move along the path. During movement along the planned path, leaf bending mechanism 22 (e.g., a rotor 64 or other device that creates a leaf bending airflow) may operate to bend leaves of crop plants in crop field 14.

In some cases, controller 16 may be configured to, under predetermined conditions (e.g., unexpected weather conditions or obstacles, or other conditions), detour from a planned path, return to a predetermined location, immediately stop operation (e.g., land UAV 60), or otherwise deviate from the planned path. In some cases, controller 16 may be configured to recalculate a modified path based on data that is acquired while moving along a previously planned path (e.g., newly detected infestation, change in wind conditions, or other data).

Concurrently with operating mobile platform 12 to move along the planned path, controller 16 may operate imager control module 18 to acquire images of crop field 14 (block 140). Acquired images may be stored, e.g., together with a time stamp, location date, or other data, e.g., as image data 42 on data storage 40.

Processor 50 of controller 16 may be configured to apply one on or more image processing techniques to acquired images. For example, application of the image processing techniques may identify regions of an imaged crop plant (e.g., leaf or stalk) in which changes in brightness or coloration, and the shapes of such regions, are indicative of an infestation. For example, an association of an appearance of plant with an infestation may be developed by application of deep learning techniques, or may be developed via review of previous studies of infestations. Such associations may be incorporated into image processing module 52.

In some cases, analysis of acquired images may yield a location of an infestation with greater accuracy than may be determined on the basis of navigation sensors alone (e.g., accuracy of a few meters using a GPS receiver). For example, analysis of a series of images may enable identification (an ordinal number) of a row of crop plants within crop field 14 (e.g., counting from a predetermined location at the edge of, or within, crop field 14). A height of imaging device 20 above the ground may be known to high accuracy, e.g., by an accurate optical or sonic altimeter, or by knowing a position of imaging device 20 on a terrestrial mobile platform 12. Application of correlation or other techniques to successively acquired images may then yield a displacement along a direction parallel to a linear row, or an azimuthal displacement along a circular row. Alternatively or in addition, a GPS or other navigation signal may be utilized to determine a position along the row. In some cases, images of various landmarks at known locations may be utilized in determining a position within crop field 14. The landmarks may include various preexisting structures (e.g., buildings, electrical poles, water pipes, tanks, or other structure that is placed independently of operation of crop monitoring system 10), or may include markers that are placed at known locations within crop field 14 to facilitate operation of crop monitoring system 10 (e.g., flags, lights, stakes, signs, beacons, or other markers).

When mobile platform 12 is a terrestrial platform, a path of motion of mobile platform 12 may be limited. For example, an irrigation machine 80 may be configured to sweep across crop field 14 along a fixed linear or circular path. A terrestrial vehicle 70 may be limited to travel between crop rows. In these cases, if imaging device 20 is fixed, path planning may not be relevant. In some cases, imaging device 20 may be configured to be displaced along a linear boom, or to be panned across an angular range, in a controllable manner. In some such cases, a planned path may indicated where imaging device 20 is to be aimed as mobile platform 12 travels within crop field 14. In other such cases, e.g., where motion of mobile platform 12 is sufficiently slow, dense coverage may be obtained of all parts of crop field 14, even in the absence of any likelihood of infestation.

In some cases, controller 16 may be configured to autonomously operate treatment unit 57 on the basis of analysis of acquired images.

According to some embodiments of the present invention, optimization of image acquisition required to detect ACRA in a field, is provided. An optimization goal may be to reduce the number of images required to successfully identify ACRA, to save processing power and processing time, to save user time, save artificial intelligence (AI) network load, etc. Optimization of the image acquisition may include detecting ACRA by acquiring an optimal number of images (referred to hereinafter as "signals"), to ascertain detection or non-detection at a given or desired probability level. Such optimization may be aimed at reducing the number of data signals and still maintaining a desired level of certainty for a given probability. Such an optimization may include determining a minimal number of signals acquired that is sufficient for obtaining a decision whether ACRA is present and identifying its location or ACRA is not present, while maintaining a desired level or accuracy or probability. A user may be allowed to set the desired level of probability.

According to some embodiments of the present invention, a probability level for an accurate decision whether ACRA exists from n number of signals acquired is given by the following equation:

$$\text{Total}(P(n)) = AI_{ac} * \sum_{k=1}^{n}\left(P_k * \left(\prod_{k=1}^{n-1}(1 - P_k)^{k-1}\right)\right) \quad (1)$$

where n is the number of signal required for a decision, k is the serial number of a current signal obtained, $AI_{ac}$ is the accuracy level of the AI engine used, and $P_k$ is the probability to detect ACRA in the current signal A modified optimization of image acquisition may be given by the following equation:

$$\text{Total}(P(n))_{improved} = 1 - \left(\prod_{i=1}^{j}(1 - \text{Total}(P(n)))\right)$$

where i is the serial number of an image of a series of images of the same field cell, and j is the total number of acquired images of that same field cell.

Figure 3B:
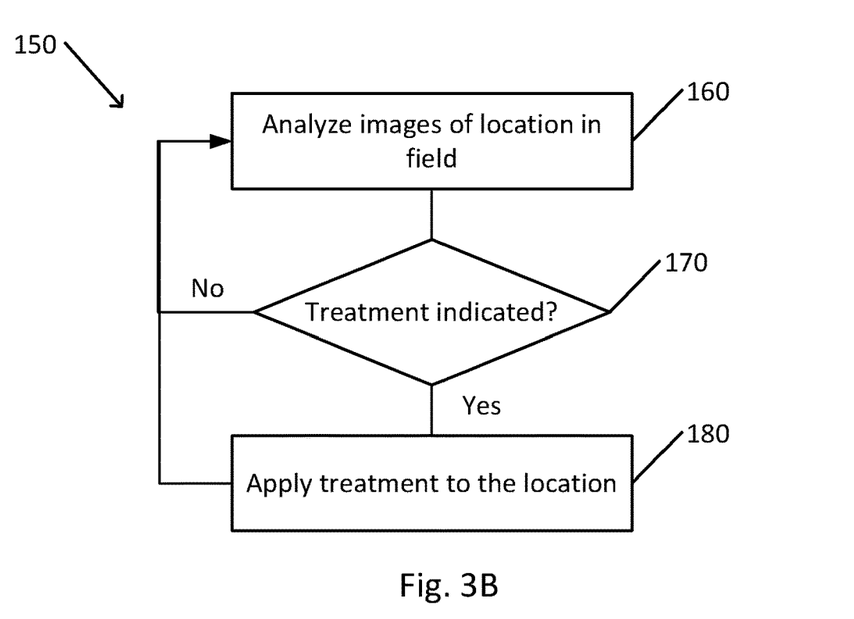
FIG. 3B is a flowchart depicting a method of autonomous crop treatment by a crop monitoring system, in accordance with some embodiments of the present invention.

FIG. 3B is a flowchart depicting a method of autonomous crop treatment by a crop monitoring system, in accordance with an embodiment of the present invention.

Crop treatment method 150 may be executed by controller 16 of a crop monitoring system 10, e.g., of a crop monitoring system 10 whose mobile platform 12 includes a treatment unit 57. For example, crop monitoring system 10 may include a terrestrial mobile platform 12 (e.g., a terrestrial vehicle 70 or an irrigation machine 80). In some cases, e.g., a mobile platform 12 that includes a UAV may be capable of lifting a sufficiently heavy payload that includes a treatment substance and a treatment unit 57.

During movement across a crop field 14, images that are acquired by imaging device 20 at a particular location in crop field 14 may be analyzed (e.g., by application of one or more image processing and image recognition techniques) for various patterns that may be indicative of infestation (block 160).

If no infestation is indicated, or if infestation is indicated but autonomous treatment is not indicated, e.g., treatment unit 57 is not configured to treat the indicated infestation (block 170), analysis of images continues (block 160).

If treatment is indicated at the location, e.g., treatable infestation is indicated or preventative treatment is indicated (block 170), treatment unit 57 may be operated to dispense a treatment substance at the location (block 180).

Figure 4A:
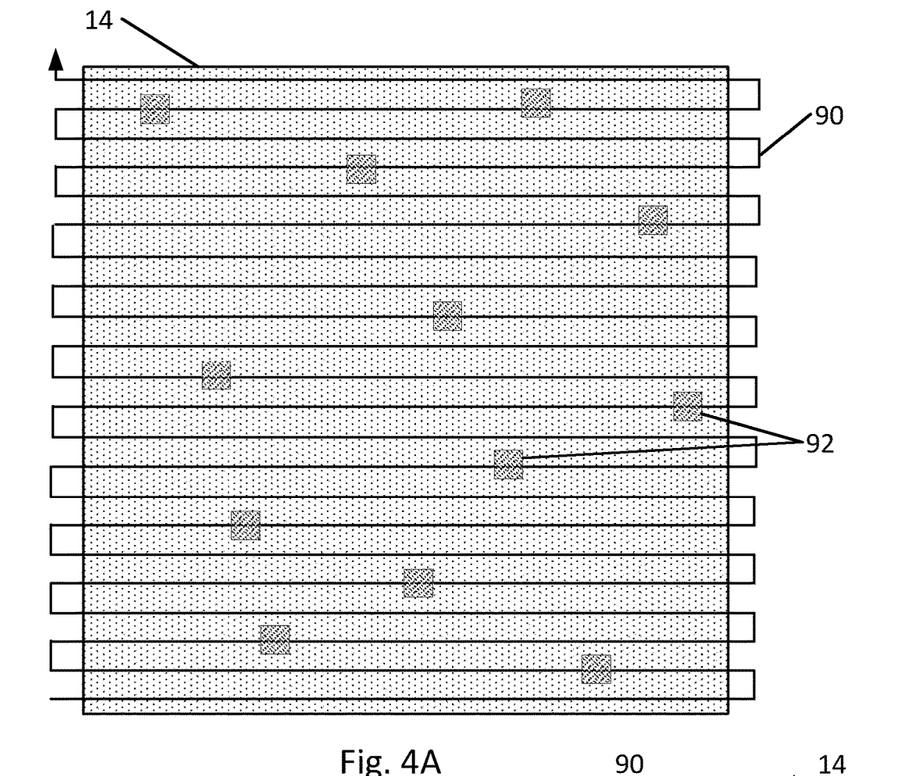
FIG. 4A schematically illustrates a basic flight path for an aerial crop monitoring system in the absence of regions of increased likelihood existing agricultural conditions requiring attention, according to some embodiments of the invention.

FIG. 4A schematically illustrates a basic scan flight path for an crop monitoring system according to some embodiments of the present invention, in the absence of regions of increased likelihood of ACRA.

In the example shown, when mobile platform 12 comprises a UAV 60, a planned basic scan flight path 90 may include a rectangular raster pattern over crop field 14. Such a rectangular raster pattern may ensure uniform coverage of crop field 14. In other examples, a basic scan flight path may include a series of concentric circles or ovals, a spiral pattern, a zigzag pattern, or another suitable pattern.

Inspection regions 92 of specific interest may be distributed across the area of crop field 14. When UAV 60 reaches a location of an inspection region 92, UAV 60 may fly in a dense pattern above that inspection region 92. For example, images that are acquired by imaging device 20 within inspection region 92 may have higher spatial resolution than images that are acquired elsewhere within crop field 14. In order to achieve different resolutions using a single imaging device 20, the field of view of imaging device 20 may be reduced. For example, the higher resolution may be achieved by increasing an optical or electronic zoom, or by flying at a lower altitude than elsewhere within crop field 14. Therefore, in order to completely cover inspection region 92, UAV 60 must fly within inspection region 92 in a denser pattern than elsewhere within crop field 14 where the resolution is lower and the field of view is larger.

The number and locations of inspection regions 92 may be determined by one or more predetermined criteria. For example, criteria may include type of crop, visibility of typical types of infestations, agronomic history of geographical region in which crop field 14 is located, topography of crop field 14, locations of obstacles to application of preventative treatments, or other ACRA. It may be noted that the number and density of inspection regions 92 on a typical crop field 14 may be much greater than the example of a pattern that is schematically shown in FIG. 4A. In some embodiments of the present invention, the flight path of the crop monitoring system may include direct substantially linear flight path between inspection regions 92, aimed at taking a short flight route between successive inspection regions 92 visited (see FIG. 4C).

Figure 4B:
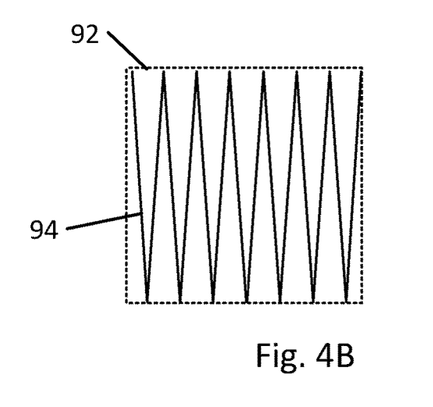
FIG. 4B schematically illustrates a flight path over an inspection region of specific interest, according to some embodiments of the invention.
Figure 4C:
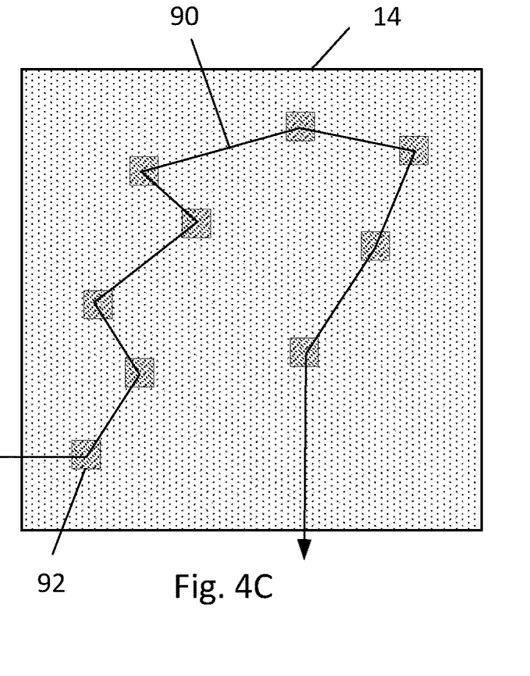
FIG. 4C schematically illustrates a flight path for a crop monitoring system, according to some embodiments of the invention.

FIG. 4B schematically illustrates a scan flight path of an inspection region of the basic flight path shown in FIG. 4A.

When UAV 60 flies within an inspection region 92, UAV 60 may be configured to fly in dense pattern 94. In the example shown, dense pattern 94 is a zigzag pattern. Such a pattern may be amenable to relatively simple and accurate programming for an autonomous UAV 60. In this example, the scan flight path is in a zig-zag form (W-like). A zig-zag scan flight path allows fast access to different parts of the scanned inspection region 92.

Alternatively or in addition, a dense pattern may include a dense rectangular raster pattern, a spiral pattern, or another pattern.

When an ACRA has been previously detected, a planned path may include dense coverage of regions into which the ACRA may spread with elevated likelihood over other regions of a field. A likelihood of ACRA may be calculated on known patterns of spread of infestation.

Figure 5:
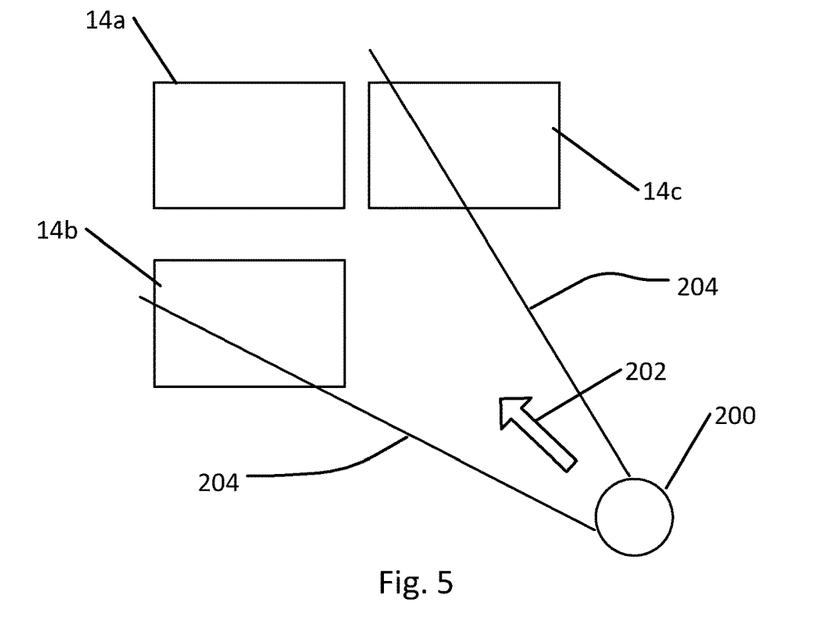
FIG. 5 schematically illustrates regions of spread of an infestation from an infested region outside of a field.

FIG. 5 schematically illustrates regions of spread of an infestation from an infested region outside of a field.

In the example shown, infestation locus 200 is located outside of crop fields 14a, 14b, and 14c. The direction of prevailing winds since the onset (or an estimated onset) of the infestation is indicated by arrow 202. In addition to spread in the direction of arrow 202, the region of infestation may widen with distance from infestation locus 200. Boundaries of the region of increased likelihood of infestation are indicated by diverging lines 204.

Therefore, in the example shown, crop field 14a lies entirely within the region of increased likelihood of infestation that is indicated by diverging lines 204. Therefore, increased density of coverage may be indicated for crop field 14a.

Parts of crop fields 14b and 14c (most of the area in the case of crop field 14b, and a minority of the area in the cases of crop field 14c) lie within the region of increased likelihood of infestation that is indicated by diverging lines 204, while other parts do not. Therefore, in the case of crop fields 14b and 14c, increased coverage density may be planned for the parts that lie between diverging lines 204, and not for the remainder of crop fields 14b and 14c.

The size of a region into which there is increased likelihood of spread of an infestation may increase with (e.g., as a monotonically increasing function of) elapsed time since the onset of the infestation. Similarly, the size of the region of increased likelihood may increase as a monotonically increasing function of increased precipitation, and the spread may be increased in the direction of prevailing winds.

Figure 6A:
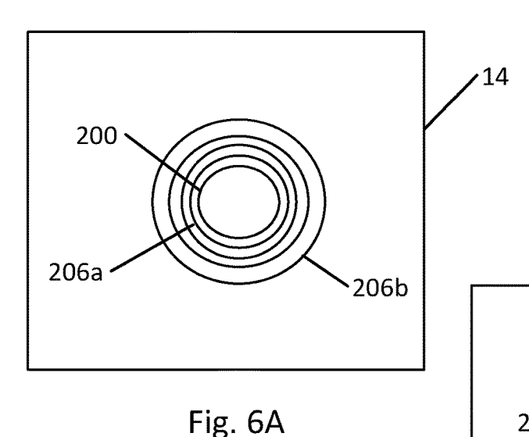
FIG. 6A schematically illustrates spread of an infestation as a function of an amount of precipitation.

FIG. 6A schematically illustrates spread of an infestation as a function of an amount of precipitation.

In FIG. 6A, the original region of infestation is indicated by infestation locus 200. After a particular period of time has elapsed since the onset of infestation, and in the absence of wind, the region of increased likelihood of infestation may increase symmetrically about and concentric with infestation locus 200. However, the radius of the region may be dependent on an amount of precipitation since the onset of infestation.

In the example shown, after minimal precipitation the region of increased likelihood may be indicated by region 206a. On the other hand, with maximal precipitation, the region of increased likelihood may be indicated by larger region 206b.

It may be noted that a dense path over region 206a, 206b, or the other unlabeled regions shown, may be a spiral path, a raster pattern, or another suitable pattern.

Figure 6B:
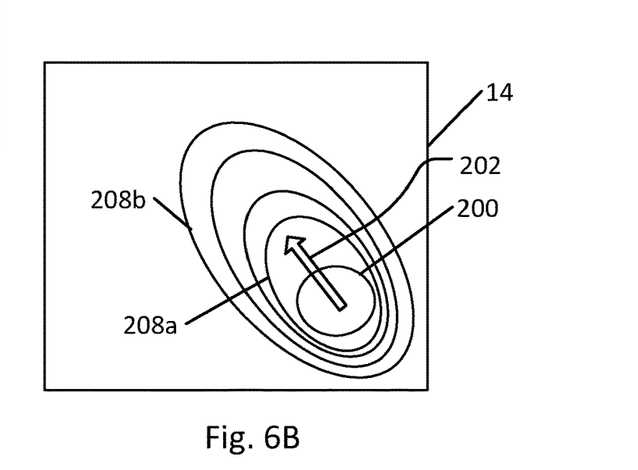
FIG. 6B schematically illustrates spread of an infestation as a function of an amount of precipitation in the presence of wind.

FIG. 6B schematically illustrates spread of an infestation as a function of an amount of precipitation in the presence of wind.

In the example of FIG. 6B, a direction of prevailing winds is indicated by arrow 202. The wind causes a region of increased likelihood of infestation to be elongated (e.g., into an elliptical or other oval shape) in the direction indicated by arrow 202. Again, the size of each region may be a function of precipitation.

In the example shown, after minimal precipitation and in the presence of wind, the region of increased likelihood may be indicated by elongated region 208a. On the other hand, with maximal precipitation, the region of increased likelihood may be indicated by larger elongated region 208b.

In this case also, a dense path over elongated region 208a, 208b, or the other unlabeled elongated regions shown, may be an elongated spiral path, a raster pattern, or another suitable pattern.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for autonomous crop monitoring, the method comprising:
providing a crop monitoring system comprising a mobile platform having one or a plurality of imaging devices configured to autonomously travel a path to scan a plurality of inspection regions in a field of the crop and obtain images of the inspection regions and a processor configured to analyze the acquired images to detect an agricultural condition that requires attention (ACRA) and determine the location of that AC;
planning a path across a field of crop plants on the basis of a calculation of a likelihood of detection of agricultural condition requiring attention (ACRA) in one or more regions of the field;
causing the mobile platform to travel along the planned path;
operating said one or a plurality of imaging devices of the system to acquire images of the crop plants as the mobile platform travels along the planned path; and
using a processor, analyzing the acquired images to detect ACRA and determine the location of that ACRA,
the method further comprising optimizing image acquisition of the crop monitoring system using the equation $$\text{Total}(P(n)) = AI_{ac} * \sum_{k=1}^{n} \left( P_k * \left( \prod_{k=1}^{n-1} (1 - P_k)^{k-1} \right) \right)$$

where n is the number of acquired images required for a given probability level of detecting ACRA, k is the serial number of a current image obtained, $AI_{ac}$ is the accuracy level of an AI engine used, and $P_k$ is the probability to detect ACRA in the current image.

2. The method of claim 1, further comprising optimizing image acquisition of the crop monitoring system using the equation:

$$\text{Total}(P(n))_{improved} = 1 - \left( \prod_{i=1}^{j} (1 - \text{Total}(P(n))) \right)$$

where i is the serial number of an image of a series of images of a same field cell of the field, and j is the total number of acquired images of that same field cell.

* * * * *